(12) United States Patent
Wessels et al.

(10) Patent No.: US 11,503,988 B2
(45) Date of Patent: Nov. 22, 2022

(54) ENDOSCOPIC DEVICE

(71) Applicant: University of Cape Town, Cape Town (ZA)

(72) Inventors: Edmund Grey Wessels, Cape Town (ZA); Sudesh Sivarasu, Kenilworth (ZA)

(73) Assignee: University of Cape Town, Cape Town (ZA)

( * ) Notice: Subject to any disclaimer, the term of this patent is extended or adjusted under 35 U.S.C. 154(b) by 552 days.

(21) Appl. No.: 16/292,650

(22) Filed: Mar. 5, 2019

(65) Prior Publication Data
US 2019/0269301 A1 Sep. 5, 2019

(30) Foreign Application Priority Data

Mar. 5, 2018 (GB) ..................................... 1803497

(51) Int. Cl.
*A61B 1/00* (2006.01)
*A61B 1/005* (2006.01)

(52) U.S. Cl.
CPC ........ *A61B 1/0058* (2013.01); *A61B 1/00006* (2013.01); *A61B 1/0053* (2013.01); *A61B 1/0055* (2013.01); *A61B 1/0057* (2013.01); *A61B 1/00103* (2013.01); *A61B 1/00135* (2013.01); *A61B 1/00137* (2013.01)

(58) Field of Classification Search
None
See application file for complete search history.

(56) References Cited

U.S. PATENT DOCUMENTS

| 4,741,326 | A | | 5/1988 | Sidall et al. | |
|---|---|---|---|---|---|
| 4,930,494 | A | * | 6/1990 | Takehana | A61B 1/00147 600/145 |
| 4,977,886 | A | * | 12/1990 | Takehana | A61B 1/0058 600/151 |
| 4,987,314 | A | * | 1/1991 | Gotanda | A61B 1/0058 250/551 |
| 5,403,297 | A | * | 4/1995 | Imran | A61B 1/0053 600/434 |

(Continued)

FOREIGN PATENT DOCUMENTS

| EP | 0533050 A1 | 3/1993 |
|---|---|---|
| EP | 0764424 A2 | 3/1997 |
| WO | 2016033403 A1 | 3/2016 |

*Primary Examiner* — Timothy J Neal
(74) *Attorney, Agent, or Firm* — The Webb Law Firm

(57) ABSTRACT

This invention relates to an endoscopic device, and more particularly but not exclusively to an endoscopic device suitable for use in diagnostic and/or surgical procedures. The endoscopic device includes a base and a shaft extending from the base. The shaft is at least partially flexible and includes a bending section that is selectively displaceable between a straight configuration and a bent configuration. The endoscopic device also includes an actuation arrangement for selectively displacing the bending section between the straight and bent positions. The actuation arrangement includes at least one actuator which is at least partially made from a shape memory alloy, and which is configured to displace the bending section of the shaft when electric current is passed therethrough. The actuator is located inside the base of the device.

11 Claims, 7 Drawing Sheets

(56) References Cited

U.S. PATENT DOCUMENTS

| | | | | |
|---|---|---|---|---|
| 5,674,182 | A | * | 10/1997 | Suzuki ............... A61B 1/00057 |
| | | | | 600/121 |
| 5,810,715 | A | * | 9/1998 | Moriyama .......... A61B 1/00078 |
| | | | | 600/139 |
| 5,810,717 | A | | 9/1998 | Maeda et al. |
| 5,897,488 | A | * | 4/1999 | Ueda .................... A61B 1/0058 |
| | | | | 600/143 |
| 6,817,974 | B2 | | 11/2004 | Cooper et al. |
| 8,137,308 | B2 | * | 3/2012 | Schultz ............. A61M 25/0136 |
| | | | | 604/95.04 |
| 8,337,521 | B2 | * | 12/2012 | Cooper ................ A61B 17/062 |
| | | | | 606/205 |
| 9,498,112 | B1 | * | 11/2016 | Stewart ................ A61B 1/0058 |
| 9,743,827 | B2 | * | 8/2017 | Yasunaga ............. A61B 1/0057 |
| 2011/0054446 | A1 | * | 3/2011 | Schultz .................... A61B 5/24 |
| | | | | 604/528 |
| 2011/0295242 | A1 | * | 12/2011 | Spivey ........... A61B 17/320016 |
| | | | | 606/1 |
| 2013/0172813 | A1 | * | 7/2013 | Caples ............. A61M 25/0136 |
| | | | | 604/95.04 |
| 2016/0174819 | A1 | | 6/2016 | Ouyang et al. |
| 2016/0367119 | A1 | | 12/2016 | Ouyang et al. |
| 2018/0368664 | A1 | * | 12/2018 | Nagda .................. A61B 1/0011 |
| 2020/0196836 | A1 | * | 6/2020 | De Jong .............. A61B 1/0053 |

\* cited by examiner

ENDOSCOPIC DEVICE

CROSS-REFERENCE TO RELATED APPLICATION

This application claims priority to United Kingdom Patent Application No. 1803497.5 filed Mar. 5, 2018, the disclosure of which is hereby incorporated by reference in its entirety.

BACKGROUND OF THE INVENTION

Field of the Invention

This invention relates to an endoscopic device, and more particularly but not exclusively to an endoscopic device suitable for use in diagnostic and/or surgical procedures.

Description of Related Art

In this specification, the term endoscopy, or an endoscopic procedure, refers to the procedure used to examine the interior of a hollow organ or cavity of the body, and may furthermore also entail a surgical procedure involving such organ of cavity. Some examples of endoscopic procedures include a hysteroscopy, laparoscopy and colonoscopy. The term endoscopy is specifically not limited to the procedure used to examine a patient's digestive tract, which is a procedure that is sometimes specifically referred to as an endoscopy.

An endoscope is used in an endoscopic procedure. An endoscope is essentially an illuminated optical, typically slender and tubular instrument, which can be used for visual examinations and diagnoses, but which can also be used to perform, or to assist in performing, surgery. An endoscope typically consists of a rigid or flexible tube, an illumination system used to illuminate the organ, cavity or object under consideration, an imaging system for transmitting an image from a lens of the endoscope to the user, and additional channels for use in the endoscopic procedure, for example a distention media channel and an operative instrument working channel. In more conventional endoscopes the imaging system is often in the form of a relay lens arrangement or a bundle of fiber optics, but in more modern and sophisticated endoscopes the imaging system is in the form of a camera that transmits an image to a screen.

Flexible endoscopes are known in the art. A flexible endoscope includes a flexible (or at least partially flexible) shaft which has a distal bending end with limited selective bending capability. In one example such a flexible endoscope includes a proximal shaft (which may be flexible or rigid) and a distal bending section, which is selectively angularly displaceable. In this example the endoscope has a pair of cords, so-called angulation wires, which run along the length of the shaft section and the bending section. Levers or a gear on the operator end, for example actuated by way of an actuation lever or an angulation knob, pull the cords differentially, resulting in the angular displacement of the bending end. A number of disadvantages are associated with this configuration. The bending end can only be displaced in a single plane, and the entire device therefore needs to be rotated should different viewing angles outside the displacement plane be required. The process is furthermore also often a two-handed process, which makes it difficult to maneuver the device whilst being simultaneously being busy with a surgical procedure. Finally, the actuation mechanism is a manual process—i.e. the angulation wires have to be tensioned manually, which is cumbersome, and which do not allow for complicated angulation wire configurations, and hence multi-directional bending of the bending section.

An example of a flexible, selectively bendable endoscopic surgical device, and more particularly a flexible wrist for such a device, is disclosed in U.S. Pat. No. 8,337,521. The wrist includes a tube having longitudinal holes or lumens distributed around a circumferential zone of the tube for receiving actuation cables or angulation wires therethrough. The tube is flexible to permit bending in pitch and yaw by pulling the cables. The hollow centre of the tube provides room for end effector cables such as gripping cables. There are typically at least four lumens, but more cables may be provided, as indicated in the specification. The proximal ends of the cables are connected to an actuator mechanism, for example such as an assembly including a gimbal plate disclosed in U.S. Ser. No. 10/187,248. This mechanism facilitates the actuation of selected cables in a coordinated manner so as to provide a bendable or steerable member in which the flexible wrist bending angle and direction can be controlled. Alternatively, a separately controlled linear actuation mechanism may be used to tension each cable, or cable pairs looped over a pulley. In both actuator configurations mentioned above, the bending is achieved by exerting a mechanical pulling force on the cables in order to tension the same, and the actuation mechanism required to give effect to accurate control of the device is therefore expensive, bulky and cumbersome, for example as shown in U.S. Ser. No. 10/187,248.

More recently, there have been developments insofar as using shape memory alloys (SMA) in endoscopes in order to improve the actuation and control of selectively bendable endoscopes. This generally involves the use of a shape memory actuator which contracts in response to an electrical current being passed therethrough.

EP0533050 discloses a bending operation apparatus designed such that a bending portion which can be bent/deformed is formed at the distal end of an insertion portion, and the proximal end portion of the insertion portion is connected to an operating portion on the manual operation side which serves to remotely control a bending operation of the bending portion. The apparatus includes three angle wires arranged in the bending portion, three actuators for independently operating the three angle wires, and a control means for arbitrarily controlling the operating amounts of the three angle wires through the three actuators. In one embodiment of this invention the actuators are in the form of SMA coils mounted inside the insertion portion of the apparatus. A significant of shortcoming are associated with the design disclosed in EP0533050 is that the SMA coils have a relatively large diameter in context of the endoscope dimensions, and the number of actuators that can be used is therefore limited if the diameter of the inserting portion is to be kept to a minimum. In addition, EP0533050 also does not disclose how the deformation of the SMA coils will occur in order to return to the bending portion to its unbent position.

Another example of a SMA based bending mechanism is disclosed in EP0764424. In this case the mechanism includes two SMA coils near the tip of the endoscope, which configuration is used to avoid buckling in the bending portion. This configuration is, however, not ideal from a miniaturisation and fabrication perspective. The degree of movement will be limited significantly if the size of the device of this kind of configuration is to be reduced. The mechanism also shows examples of achieving multiple directional bending by placing SMA coils at equal intervals between joint along the inner tube. Again, the use of multiple SMA coils complicates the design, and also adds to the general size of the mechanism.

In order further to illustrate the shortcomings of existing endoscopes, reference is now made to specific shortcomings associated with hysteroscopies. A hysteroscopy is a procedure that entails using an endoscopic device, in this case a hysteroscope, inserted through the vaginal canal and cervix, to directly inspect the inside of the uterus. Surgical instruments can also be inserted through the hysteroscope's working channel to perform operative procedures. Most hysteroscopes have rigid shafts, which cause immense discomfort and which requires the patient to undergo general anesthesia, thus necessitating the procedures to be performed in the operating theatre. These hysteroscopes also require bulky additional equipment for providing light sources and visual interfaces, which limit the mobility of the entire system. These factors result in very high costs for what is a relatively simple and minimally invasive procedure. As mentioned above, endoscopic device with limited angular maneuverability is known in the art, but even these devices do not provide sufficient flexibility when performing a hysteroscopy. Due to the very nature of an endoscope it will be readily apparent that there will always be a need to reduce the size of these devices, in particular the diameter of the insertion sections. In present configurations, particular those where the actuating means are located in the insertion section, a reduction in size is however often associated with a reduction in functionality, which is also not ideal.

A further disadvantage associated with existing endoscopes in general is that almost the entire device has to be sterilized after use. The sterilization process poses a risk of damage to the components of the device, and also reduces the lifespan of the device. It has been proposed for parts of endoscopic devices to be disposable in order to reduce the need for sterilization, and also for a disposable sheath to be fitted over the central body of the endoscope, thus reducing the need for the serialization of components in use covered by the sheath. For example, US2016/0367119 discloses a handheld surgical endoscope that has a disposable, single-use handle, cannula and distal tip. The distal tip, however, includes the LED illumination and an imaging module that feeds live video to a re-usable display module that connects off-axis to the disposable handle. It will be appreciated that it is not ideal for the entire tip, including the camera and light, to be disposable, as the tip constitutes a costly component. Similarly, US2016/0174819 discloses an endoscopic device having a re-usable portion including a handle, electronics and an integrated display screen while a fluid hub, and a single use portion including a cannula which includes a CMOS imaging module and LED lighting. It will be appreciated that in both the above examples, it is not ideal for the entire tip or cannula, including the camera and light, to be disposable, as this does not make financial sense.

It is accordingly an object of the invention to provide a surgical device that will, at least partially, alleviate the above shortcomings.

It is also an object of the invention to provide a surgical device which will be a useful alternative to existing surgical devices.

SUMMARY OF THE INVENTION

According to the invention there is provided an endoscopic device including:
a base;
a shaft extending from the base; wherein the shaft is at least partially flexible and includes a bending section that is selectively displaceable between a straight configuration and a bent configuration; and
an actuation arrangement for selectively displacing the bending section between the straight and bent positions;
wherein the actuation arrangement includes at least one actuator which is at least partially made from a shape memory alloy, and which is configured to displace the bending section of the shaft when electric current is passed therethrough;
characterized in that the actuator is located inside the base of the device.

There is provided for the actuator to be in the form of a helical coil or spring.

In one embodiment there is provided for an angulation wire to extend from the actuator towards the bending section of the shaft, in order for displacement of the actuator to be transmitted to the bending section.

A first end of the angulation wire may be secured to or relative to the actuator, and the second end of the angulation wire may be secured to a distal end of the shaft.

There is provided for a pivotable arm to be located between the actuator and the angulation wire, with an end of the actuator and an end of the angulation wire secured to the pivotable arm in order for actuation of the actuator resulting in displacement of the pivoting arm, with the pivotable arm in turn displacing an end of the angulation wire.

There is provided for the pivotable arm to be connected to a rotary measurement sensor, such as a potentiometer, that allows the control system of the bending mechanism to determine the current position of the bending section.

There is also provided for a biasing means to be located in the bending section in order to support the bending section and urge it towards an unbent configuration.

The biasing means may be in the form of a helical spring.

Preferably the actuating arrangement includes at least two actuators in the form of two helical springs.

A further feature of the invention provides for the shaft to include a non-bending section which is at least partially flexible, and which can be configured between a flexible condition in which some flexibility is present in the non-bending section, and a stiff condition in which substantially no flexibility is present in the non-bending section.

There is provided for at least one shape memory alloy stiffening wire to extend from the base into and along the non-bending section, with an end of the stiffening wire being secured to an end of the non-bending section, in order for contraction of the stiffening wire to result in contraction of the non-bending section of the shaft, thus resulting in the non-bending section becoming rigid.

In one embodiment of the invention the actuator is located inside a hollow bore provided in the base, with a first end of the biasing means secured relative to the base, and a second end of the biasing means secured to an end of the angulation wire.

There is provided for the shape memory alloy to be a nickel titanium alloy, and more particularly nitinol.

A further feature of the invention provides for the endoscopic device to include an imaging system and an illumination arrangement.

The imaging system may include a camera located at a distal end of the shaft.

The illumination arrangement may include a light source, for example a LED, located at a distal end of the shaft.

There is provided for the shaft to include a hollow core suitable for receiving wiring for the imaging system and the illumination arrangement.

The angulation wires may be spaced apart about the core at equal intervals.

A still further feature of the invention provides for the endoscopic device to include a disposable sheath configured and dimensioned to fit around the shaft.

There is provided for the sheath to be made of a flexible material.

The sheath may be a tubular element having a hollow bore suitable for receiving the shaft.

The sheath may also include at least one, preferably at least two, enclosed channels extending longitudinally along the periphery of the sheath.

Another feature of the invention provides for the endoscopic device to include a control arrangement for controlling the actuation arrangement, the control arrangement including a control system and a control knob, wherein displacement of the control knob results in the control system causing electricity to be conducted through a selected actuation element.

The control knob may be in the form of a thumb stick provided on the base.

According to a further aspect of the invention there is provided a method of bending a bending section of an endoscopic device, the method including the steps of:
providing an endoscopic device as described above; and
causing electricity to be passed through an actuator of the endoscopic device.

According to a still further feature of the invention there is provided a disposable sheath, suitable for use with an endoscopic device, the disposable sheath including an elongate, flexible tubular body having a hollow bore suitable for receiving the shaft, and at least one enclosed channels extending longitudinally along the periphery of the sheath.

The sheath is furthermore characterised in that it does not include a camera and/or a light source.

BRIEF DESCRIPTION OF THE DRAWINGS

An embodiment of the invention is described by way of a non-limiting example, and with reference to the accompanying drawings in which.

DETAILED DESCRIPTION OF INVENTION

Figure 1:
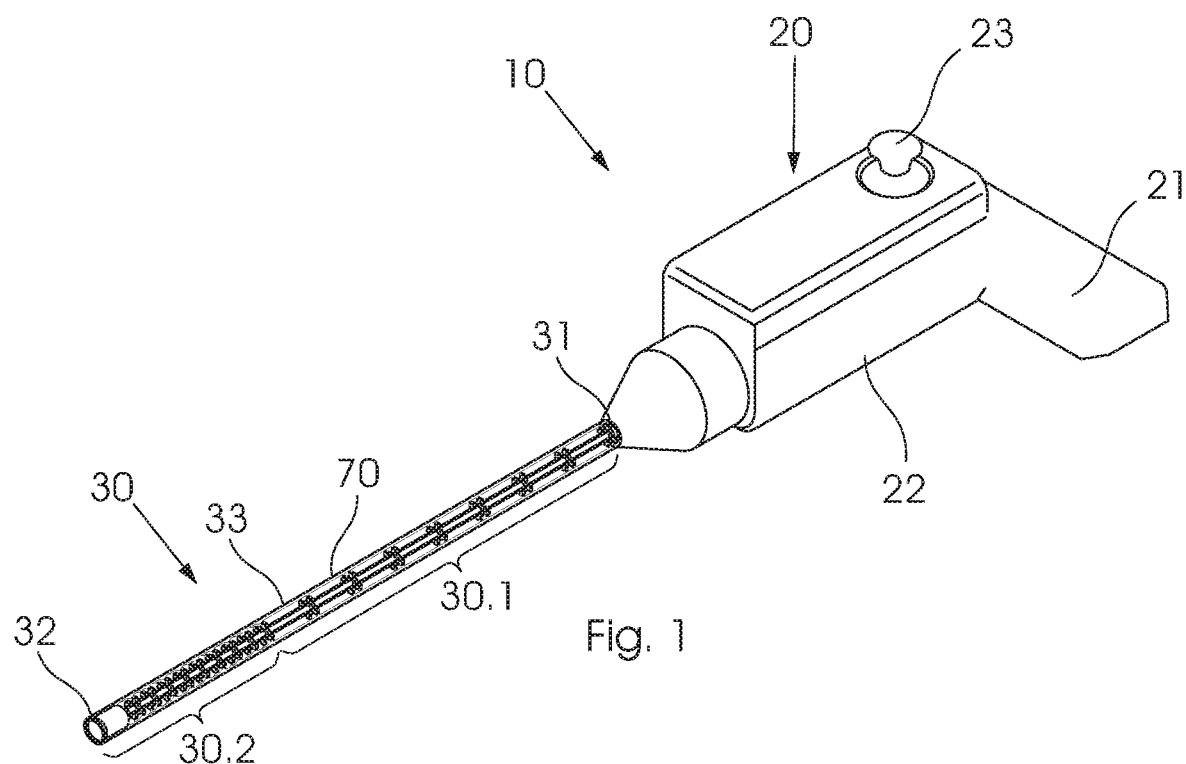
FIG. 1 is a perspective view of the endoscopic device in accordance with a first embodiment of the invention.
Figure 2:
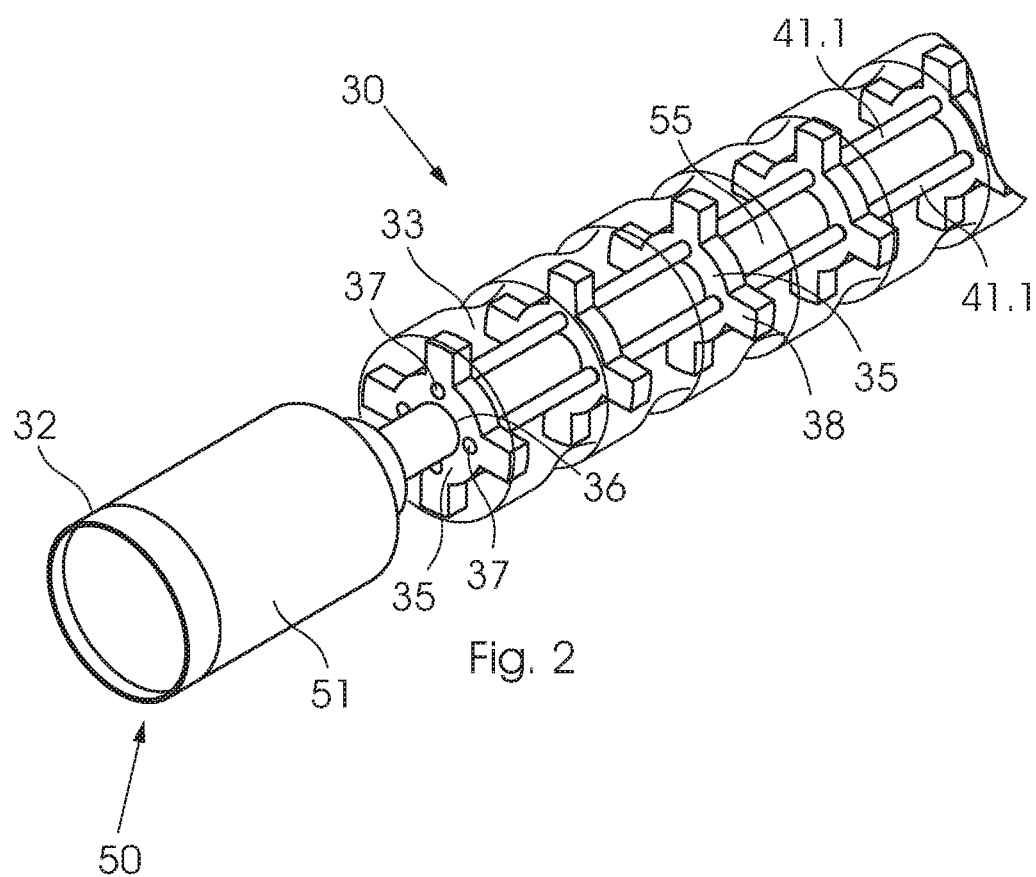
FIG. 2 is a perspective view of a distal end of a shaft of the endoscopic device of FIG. 1, excluding a disposable sheath that, in use, fits around the shaft.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings and are thus intended to include direct connections between two members without any other members interposed therebetween and indirect connections between members in which one or more other members are interposed therebetween. Further, "connected" and "coupled" are not restricted to physical or mechanical connections or couplings. Additionally, the words "lower", "upper", "upward", "down" and "downward" designate directions in the drawings to which reference is made. The terminology includes the words specifically mentioned above, derivatives thereof, and words or similar import. It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Referring to the drawings, in which like numerals indicate like features, a non-limiting example of an endoscopic device in accordance with the invention is generally indicated by reference numeral 10.

Reference is first made to the endoscopic device as shown in FIGS. 1 to 10.

The endoscopic device 10 includes a base 20, and an elongate shaft 30 extending from the base 20. The endoscopic device 10 can furthermore be connected to a display screen (not shown), for example the screen of a smartphone or any other digital display. For the purposes of this description the display screen, and the method of communication between the endoscopic device 10 and the display screen, is not described in detail, as it does not form part of the gist of the invention.

The base 20 of the endoscopic device 10 can generally be divided into a body 22, and a handle 21 extending from the body 22. A control knob 23, which in this example takes form of a thumb stick, is located on the body 22, and is conveniently accessible by a thumb of a user when the user engages the handle 21 of the endoscopic device 10. A central bore 24 (seen in FIGS. 7 and 10) extends into the body 22 of the base 20, and defines an auxiliary channel for receiving wiring that extends from the imaging system 50 and the illumination arrangement 60 as is discussed in more detail below. A plurality of actuation bores 25 are also provided in the body 22, and are radially spaced apart from the central bore 24. The actuation bores 25 are spaced around the body 22 at equal intervals, and are parallel to the central bore 24. In this particular example, four actuation bores 25 are provided, and are located at 90° intervals relative to one another. In use, angulation elements 41 extend through the actuation bores 25, as is discussed in more detail below.

The insertion section or shaft 30 of the endoscopic device 10 is of an elongate configuration, and can be functionally divided into a non-bending section 30.1, and a bending section 30.2. It should be noted that in this specification the term "non-bending" denotes a part of the shaft that cannot be remotely deformed in a controlled manner. However, this part of the shaft can still be flexible and can therefore, if it is indeed flexible, still be bent upon insertion of the endoscopic device 10 should that be a requirement. In other embodiments, the non-bending section 30.1 may also be completely rigid. The non-bending section may also be selectively adjusted between rigid or partially flexible states, as illustrated in the second embodiment of the invention described in more detail below. The shaft 30 has a proximal end 31 that is, in use, connected to the base 20, and a distal end 32 which is in use the terminal end of the shaft furthest away from the base 20.

Figure 8:
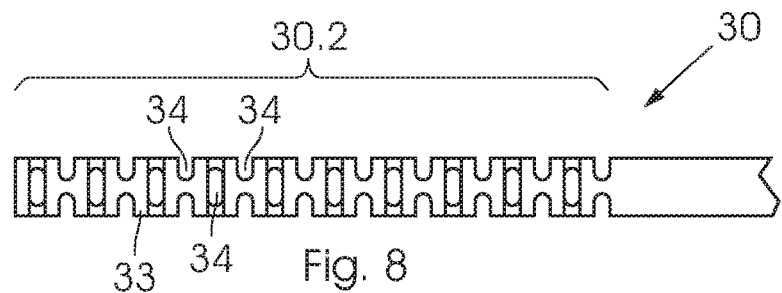
FIG. 8 is a side view of a tube forming part of the shaft of the endoscopic device.
Figure 9:
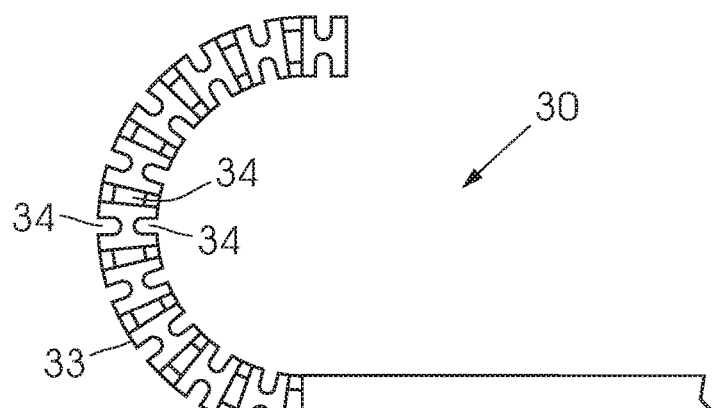
FIG. 9 is a side view of the tube of FIG. 8 in which a bending section of the shaft has been bent.

In this embodiment the shaft 30 includes a central tube 55 that extends through central openings 36 provided in adjacently located, spaced apart spacers 35. Each spacer 35 is substantially star or cross-shaped, and includes a plurality of spokes 38 extending radially outwardly from a proximal zone of the spacer 35. In use, the outer ends of these spokes 38 support a hollow outer tube 33 extending along the length of the shaft 30. The outer tube 33 may be made from an at least partially flexible material. Notches or grooves 34 are provided in the tube 33, and more particularly in the bending section 30.2 of the tube, as is seen in FIGS. 8 and 9. These grooves or notches 34 enable the outer tube 33, and hence the shaft 30, to be easily bendable in the bending section 30.2. The grooves or notches 34 are furthermore staggered so as to enable the outer tube 33, and hence the shaft 30, to be displaceable in different directions. The grooves or notches 34 are typically in the form of circumferentially orientated slots that do not extend more than half of the circumference of the tube 33. It will be appreciated that the configuration of the shaft may change, provided the construction is such that the shaft is at least partially bendable, in particular at the bending section. Instead of a tubular element with notches, the shaft may for example also include a plurality of tubular segments that are located end to end, and which are at least partially angularly displaceable relative to one another.

A plurality of auxiliary holes 37 are also provided in each spacer 35. These auxiliary holes 37 are radially outwardly located from the central cavity 36 of the spacer 35, and in this example are located at the base of each spoke 38 of each spacer 35. The auxiliary holes 37 are configured and dimensioned for receiving angulation wires 41.1 extending along the length of the shaft 30. In the illustrated embodiment four auxiliary holes 37 are provided, but the number of holes will depend on the number of angulation elements 41 used, as is discussed in more detail hereinbelow.

The endoscopic device 10 includes an actuation arrangement 40 which enables the bending section 30.2 to be selectively displaced in a desired direction, and to a desired extent. The actuation arrangement 40 includes a plurality of angulation elements 41, which are in use actuated by passing an electric current therethrough. In this embodiment, each angulation element 41 comprises an angulation wire 41.1 as well as an actuator 41.2, as can be best seen in FIG. 7. Each actuator 41.2 in this example takes the form of a helical coil or spring, and is located in an auxiliary bore 25 of the base 20, with a first end of each spring secured, and hence stationary, relative to the base 20. An end of each angulation wire 41.1 is in turn secured to a freely displaceable opposite end of each actuator 41.2, and extends from the auxiliary bore 25 in the body 22 into the shaft 30 of the endoscopic device 10. The angulation wire 41.1 runs along the length of the shaft 30, and more particularly extends through the auxiliary holes 37 provided in the spacers 35 of the shaft 30. A distal end of each angulation wire 41.1 is secured relative to the distal end 32 of the shaft 30. The configuration of each angulation element 41 is such that the bending section 30.2 of the shaft 30 will be displaced if the effective length of an angulation element 41 is reduced. More particularly, the bending section 30.2 will be displaced towards the angulation element 41 that is being contracted.

There is provided for either the angulation wires 41.1 or the actuators 41.2, or both the angulation wires 41.1 and the actuators 41.2 to be made from a SMA. In a preferred embodiment only the actuators 41.2 are made from a SMA, and electricity is, in use, only passed through the actuators 41.2, and not through the angulation wire 41.1. In one embodiment the SMA is a nickel titanium alloy, and more particularly nitinol. This results in the angular angulation element 41 contracting when electric current is passed therethrough. When such an angulation element 41 contracts (denoted by A in FIG. 10), an opposing angulation element 41 is caused to extend (denoted by B in FIG. 10). The extended and contracted elements will maintain the position they are in once the circuit is interrupted. The bending section will again straighten when the extended angulation element is activated, causing it to contract and the opposite contracted element to extend.

Figure 6:
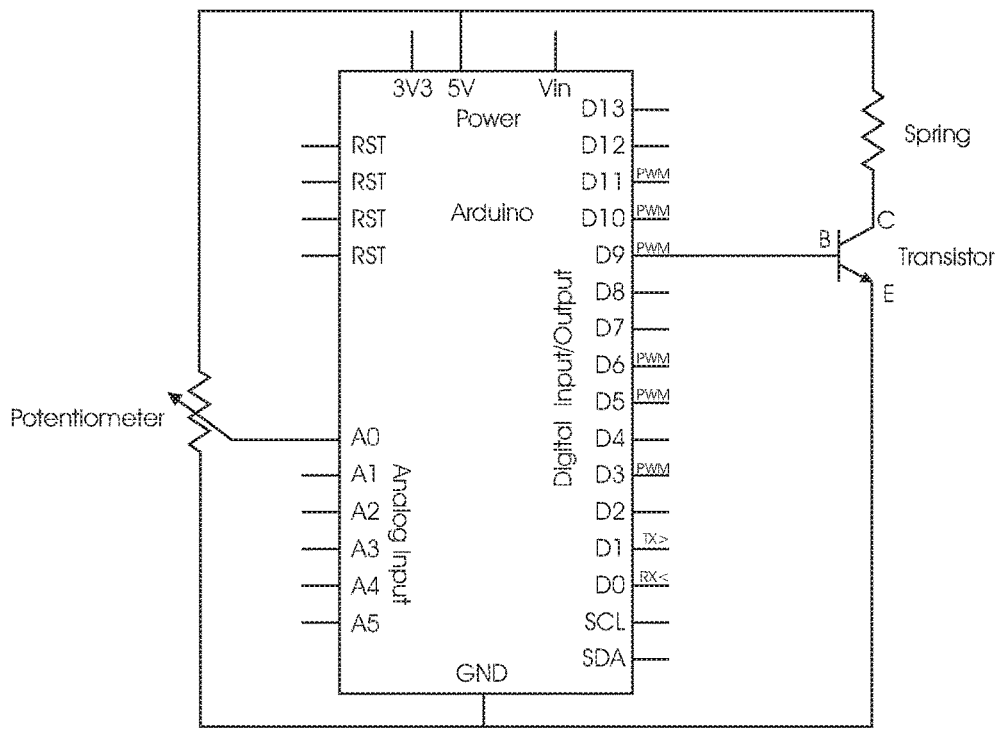
FIG. 6 is a schematic representation of a control circuit of the endoscopic device.
Figure 7:
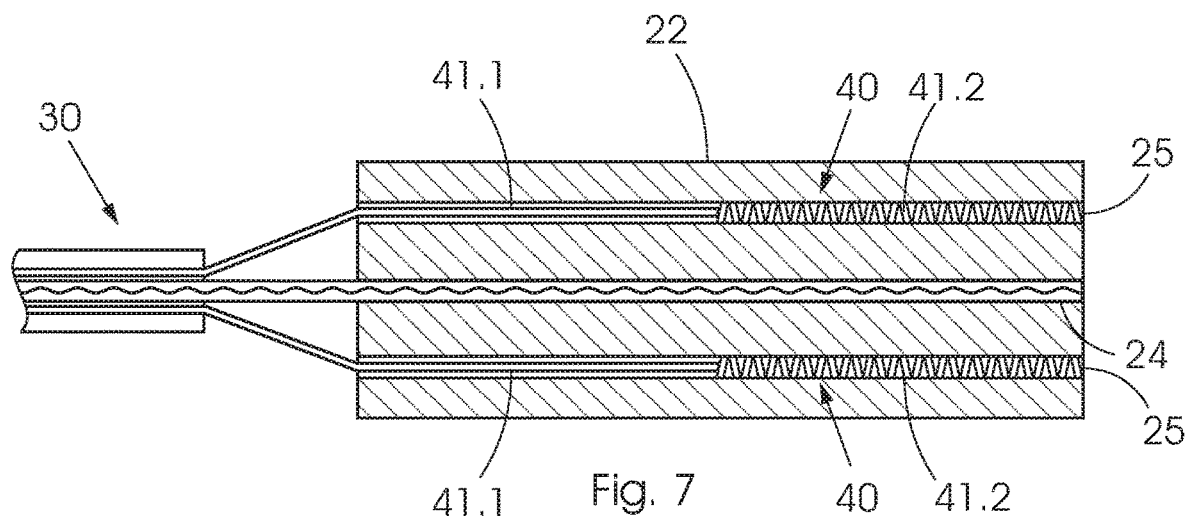
FIG. 7 is a cross-sectional side view of a front part of the base of the endoscopic device of FIG. 1.

A control system 80, shown in FIG. 6, controls the displacement of the endoscopic device 10, and converts the relative position of the control knob or thumb stick 23 to an appropriate electrical current passed from a source of electricity through the relevant angulation element 41. In this example, the control system consists of an Arduino Nano microcontroller and a thumb-stick potentiometer and transistor, which then controls the angulation element, and in this particular example the nitinol spring 41.2. The design and construction of the control system may take many different forms, but the salient feature is that movement of some control appendix (e.g. the control knob) is converted into an electrical current that is passed through a corresponding actuator.

The endoscopic device 10 also includes an imaging system 50 and an illumination arrangement 60 allowing the user the necessary visual feedback required to utilise the device. In this embodiment the imaging system 50 is in the form of a camera 51 mounted at a distal end 32 of the shaft 30, and the illumination arrangement 60 includes at least one LED, which is also located at a distal end 32 of the shaft and which illuminates the area to be observed by the camera 51. Importantly, the camera and the LED are mounted on the shaft 30 of the device, and not on a disposable sheath 70 surrounding the shaft.

Figure 3:
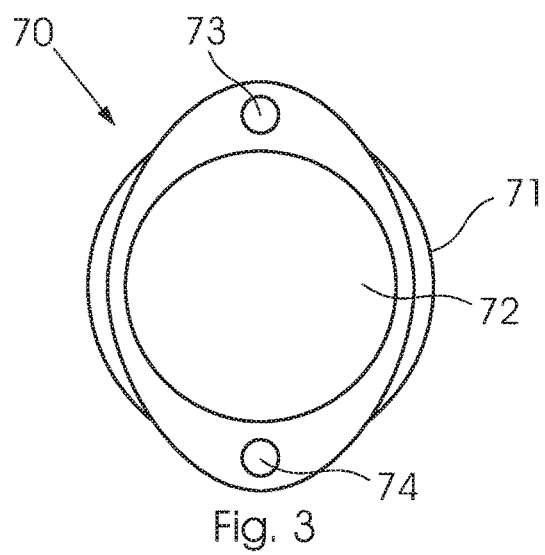
FIG. 3 is an end view of the distal end of FIG. 2, also including the disposable sheath.
Figure 4:
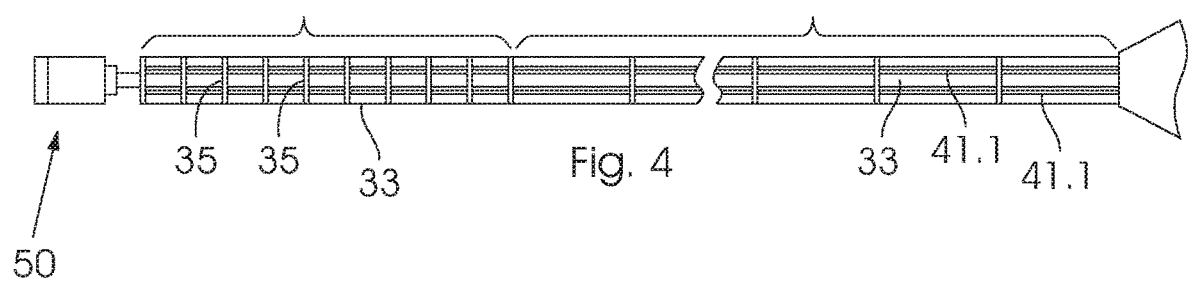
FIG. 4 is a side view of the shaft or insertion section of the endoscopic device of FIG. 1, excluding the disposable sheath that, in use, fits around the shaft.
Figure 5:
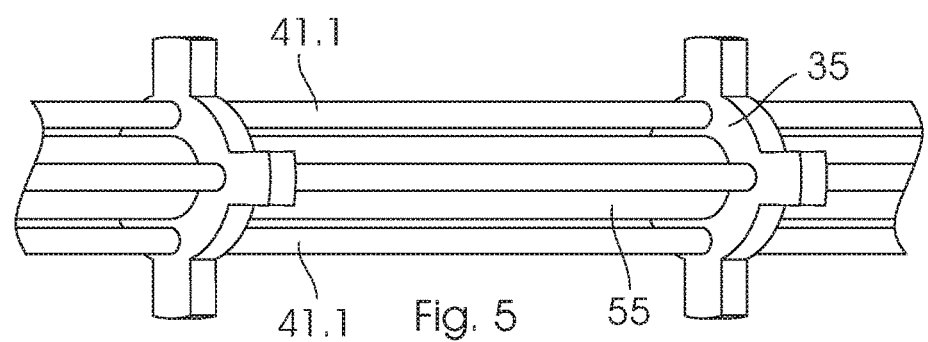
FIG. 5 is an enlarged perspective view of part of the shaft of FIG. 2, excluding a tubular member forming part of the shaft.

The disposable sheath 70 is locatable on the shaft 30, and in use covers the shaft, the imaging system 50 and the illumination arrangement 60. This sheath 70 can be removed after the endoscopic device 10 has been used, and is disposable because no expensive components form an integral part of the sheath. As shown in FIG. 3, the sheath is in the form of a tubular body 71 adapted snugly to fit over that shaft 30 of the endoscopic device 10. A lens 72 is provided at the end of the sheath 70 and in use is located operatively in front of the camera 51. A working channel 73, for receiving instruments, and a distension immediate channel 74, through which distension media can be injected, also form part of the sheath 70. The disposable sheath covers the entire shaft, isolating it from the surrounding environment and ensuring sterility. The sheath is therefore made from a material that is suitable for sterilization and medical use. The purpose of this is to allow the flexible shaft and base to be reusable, whilst require minimal sterilization after use.

Figure 16:
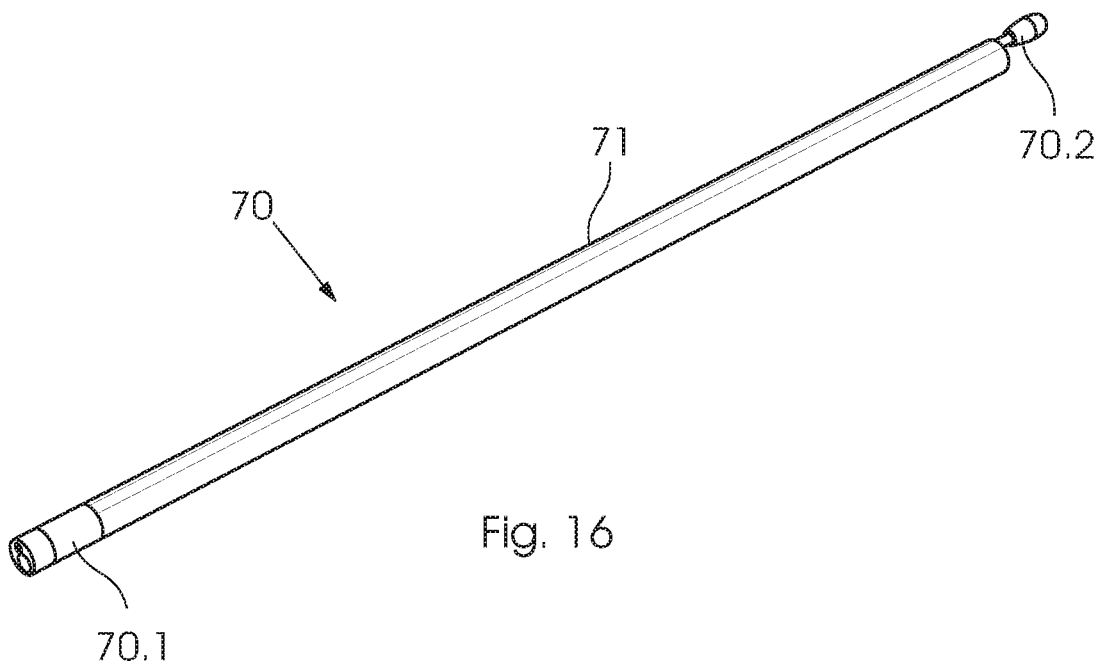
FIG. 16 is a perspective view of a disposable sheath for use with the device.
Figure 17:
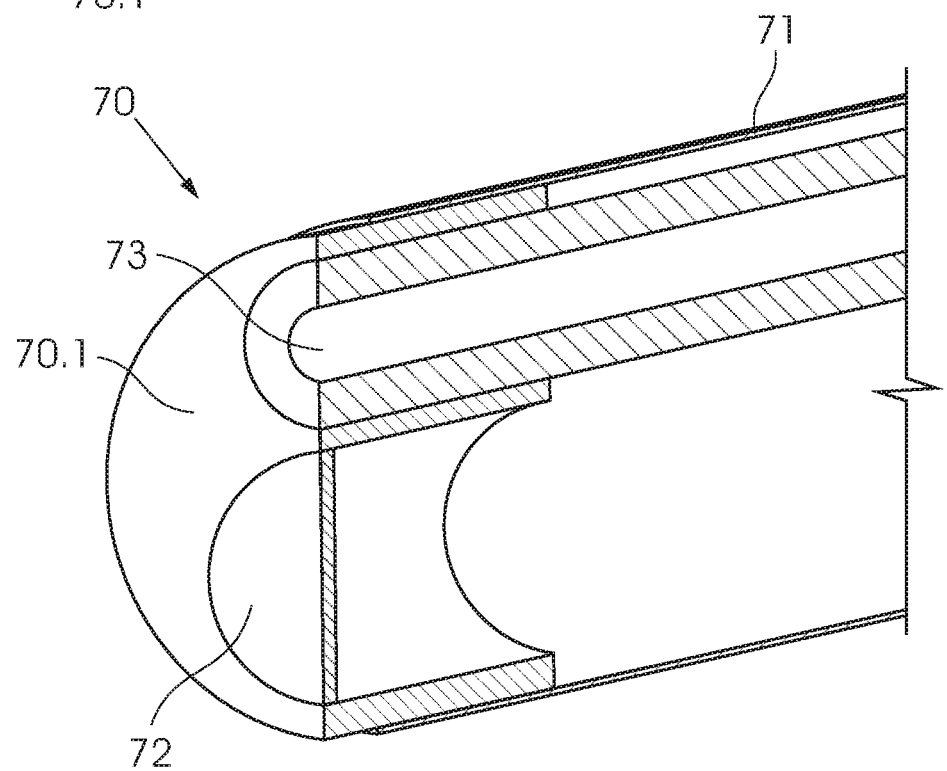
FIG. 17 is an enlarged cross-sectional view of an end cap of the sheath of FIG. 16.

A further adaptation of the disposable sheath is shown in FIGS. 16 and 17. In this embodiment the sheath 70 comprises separate components which, although requiring some pre-use assembly, will be simpler and cheaper to produce. The sheath 70 includes an independent flexible, tubular section 71, with an end cap 70.1 provided at one end of the tube, and a further internal tube extending between the end cap 70.1 and the open end of the tubular section 71. A valve 70.2 is provided at the open end of the internal tube. A tip of the shaft 30 is inserted into the tubular section 72 from the end where the valve 70.2 is located, and is pushed all the way to the end cap 70.1 where it is locked in place. A lens 72 is provided in the cap, and isolates the shaft 30 from the working environment while ensuring image clarity and light is transferred. The internal tube acts as a distension medical channel, and is in flow communication with a complementary distension outlet 73 provided in the end cap 70.1. A distension source (not shown) is in use attached to the valve 70.2, in order for distension media to be conveyed along the internal tube to the distension opening 73 at the distal end cap 70.1. The primary reusable device therefore never comes into contact with either the distension media or working environment. The sheath shown in the drawings include two internal channels—one for the shaft of the device, and one for distension media, but it will be appreciated that one or more additional channels can be provided, with each such channel being in flow communication with an appropriate opening in the end cap 70.1. It is important to note that the sheath used in this invention is a disposable sheath, and is not a permanent sheath as is associated with the prior art.

The use of the endoscopic device 10 is now described with specific reference to a hysteroscopy. A hysteroscopy procedure involving the endoscopic device 10 commences by attaching the sterilized sheath 70 over the bending shaft 30. A dispenser of distention media is then inserted into the designated channel 74 on the sheath 70 and the outflow is tested. The device 10 is then switched on, and the connected tablet/smartphone (not shown) displays the camera's visual feed. The shaft 30, and hence the camera 50, is then inserted into the vaginal canal and guided through while distention media is used to open the canal. When the cervix is reached, an inspection of the entrance can be conducted before the distal end 32 of the shaft 30 is guided through the cervix into the uterus. Once inside the uterine cavity, the operator can control the bending of the shaft to visualise the entire cavity without having to maneuver the entire device.

Figure 10:
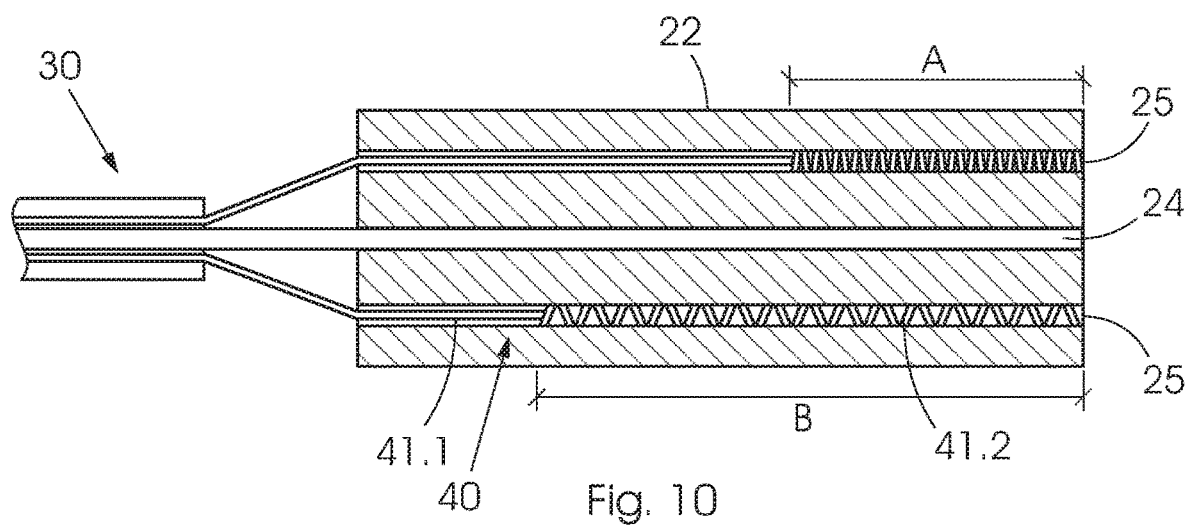
FIG. 10 shows the base of the endoscopic device as depicted in FIG. 7, when the shaft is in a bent configuration.

The bending process is broken up into three steps, which are user input, spring actuation, and finally bending of the shaft. The user activates the bending of the shaft in the chosen direction by pushing the thumb-stick 23. The potentiometer of the thumb-stick then sends an analogue variable to the microcontroller, which variable increases to a maximum value corresponding to how much the thumb-stick is displaced. The analogue variable is then converted into to digital value, which determines the power supplied through use of the Pulse Width Modulator (PWM) on the microcontroller. The transistor is activated by the PWM, which in turn activates the actuator 41.2 in the circuit. The actuator then contracts until the thumb-stick is released. During this contraction the corresponding wire is pulled, causing the notched part of the bending section 30.2 to bend in the specified direction. When an actuator contracts, the actuator on the opposing side extends, which in turn enables the shaft to return to its original state by contracting the opposing actuator, as shown in FIG. 10.

The resulting bending motion varies based on how much the actuator contracts. FIG. 9 shows the shaft bending up to 180°, with any displacement between 0° and 180° being feasible. Images of any significant areas identified can be recorded and if necessary, an operative instrument can be inserted, through the working channel 73, to perform a procedure. Once the diagnosis or operation is completed, the operator can slowly withdraw the device, while its flexibility ensures easy extraction. After removal, the sheath is detached and disposed while the system is cleaned with sterilizing wipes. The system is then stored while the images captured are downloaded from the tablet/smartphone for future reference.

A second embodiment of the invention is now described with reference to FIGS. 11 to 15. The basic principle and operating methodology remains the same, and the discussion that follows below will focus on some of the salient differences only.

Figure 11:
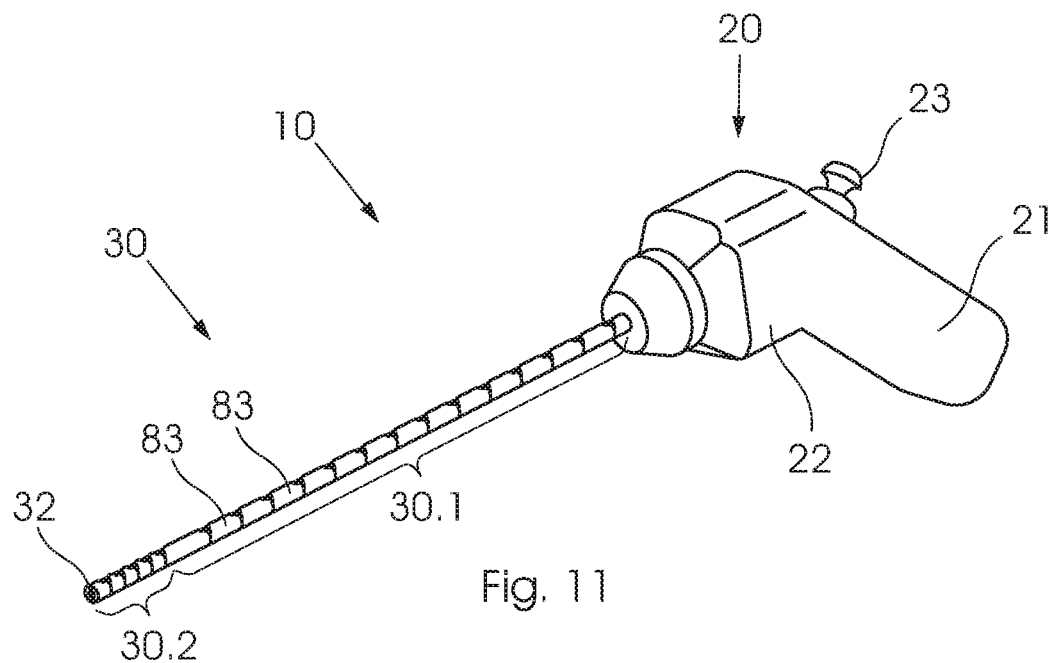
FIG. 11 is a perspective view of the endoscopic device in accordance with a second embodiment of the invention.
Figure 12:
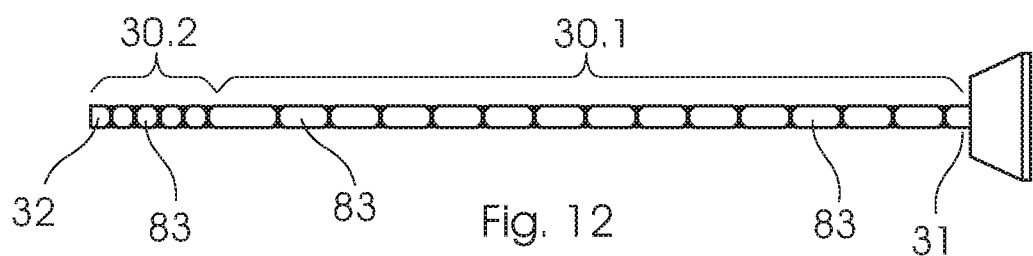
FIG. 12 is a side view of the shaft or insertion section of the endoscopic device of FIG. 1.

As is seen in FIGS. 11 and 12, the shaft or insertion section 30 still comprises a bending section 30.2 and a non-bending section 30.1. The bending section 30.2 is controlled by the actuating arrangement 40 located in the base 20 of the device and acts similarly to the previous design. The non-bending section 30.1 of the shaft is somewhat flexible (as may also be the case with the first embodiment), however in this case the non-bending section 30.2 can be activated or adjusted to become substantially rigid. When activated, it maintains whichever position it is in at the moment of activation. Accordingly, if the non-bending section is slightly angularly displaced, it will stay in that position and become substantially rigid when activated. This allows the shaft to easily navigate channels when flexible, and by stiffening it prevents buckling when bending of the tip is initiated. The activation capability will be discussed in more detail with reference to FIG. 13 below.

Figure 13:
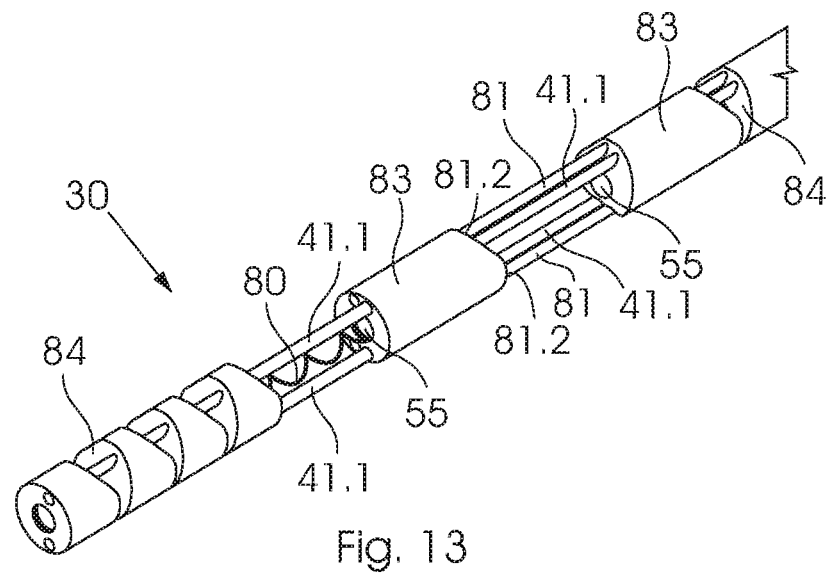
FIG. 13 is a perspective view of a front end of the shaft or insertion section, excluding the disposable sheath that, in use, fits around the shaft, and also excluding some sections of the shaft in order more clearly to show the inside of the shaft.

FIG. 13 shows a more detailed view of the redesigned shaft or insertion section 30. The shaft 30 still includes a central tube or passage 55 allowing for instrumentation. However, a compression spring 80 is now also located in this channel, and is referred to as a guide spring. The guide spring is located in the bending section 30.2 of the shaft and ensures that even bending occurs, while at the same time preventing any kinking of wire inside the channel. The spring 80 also aids in returning the bending section 30.2 to its straight position after bending. In this embodiment, ends of the angulation wires 41.1 are still connected to the distal end of the bending section, with opposite ends being connected to the bending actuating arrangement 40 in the base 20 at the other end. The angulation wires may be made from a SMA for the sake of convenience, but does not need to have the SMA functionality. In this embodiment, no current will be passed through the angulation wires 41.1, and they merely act as transmitters of displacement emanating from the actuators 41.2. There is therefore also specifically provided for the angulation wires not to be made from SMA. The structure of the shaft 30 includes a number of tubular segments 83 with convex ends, thus resulting in tapering gaps 84 being formed between adjacent segments. The gaps between the segments allow for some angular movement between these segments.

Two additional wires (in this case SMA wires referred to as stiffening wires 81), are provided in the non-bending section 30.1 of the shaft. As mentioned above, in context of this specification "non-bending" does not mean that this section cannot bend at all, but merely indicates that this section is not the part that is bend in a controlled and directed manner. This section will preferably still be somewhat flexible to assist in manoeuvring the insertion section, but it would also be beneficial if this section could be completely rigid when needed. The stiffening wires 82 provides this functionally. Two stiffening wires 82 are located in the non-bending section of the shaft 30, and terminal ends are connected to a last segment 83 of the non-bending section 30.1. Opposite ends 81.1 of the stiffening wires are secured to the base 20, and are connected to an electrical source. Notably, the stiffening wires are not connected to the actuation arrangement 40. When relaxed, the wires 81 allow the non-bending section of the shaft to bend as a result of the slack provided between the segments 83. However, once activated, the wires 81 contract, pulling the segments 83 together which results in the non-bending section 30.1 stiffening. These SMA wires do no cause any bending to occur, and instead only provide a contraction force to pull segments together. The operation of the device therefore remains unchanged from the previous design, with only the activation of the SMA wires being added.

Figure 14:
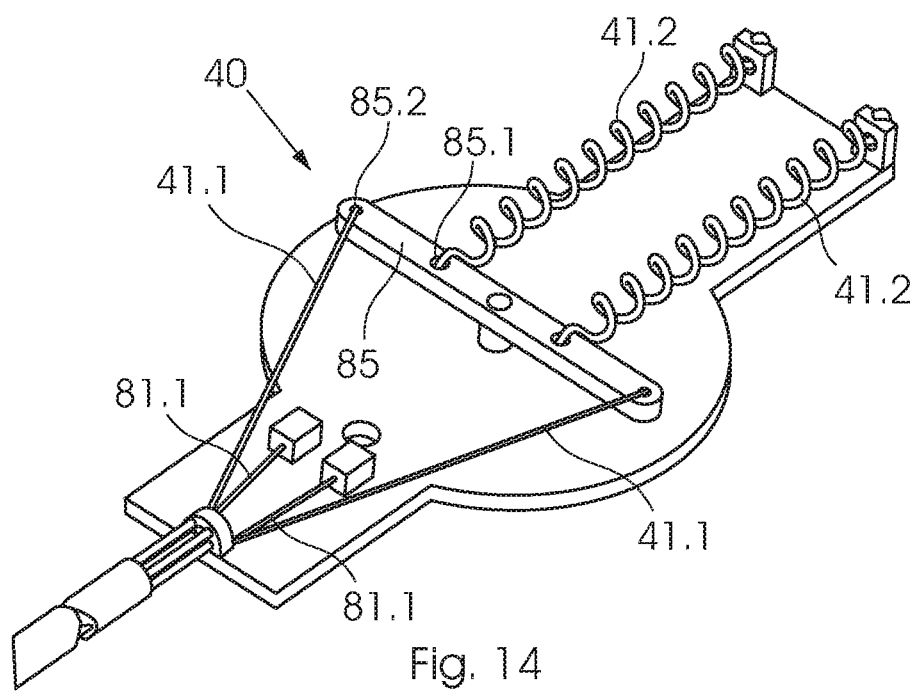
FIG. 14 is a perspective view of an actuation arrangement located inside the base of the endoscopic device.

The actuation arrangement or bending mechanism 40 housed within the base 20 of the device 10 is shown in FIGS. 14 and 15. The figures show two SMA actuators in the form of springs or coils 41.2 which allow for two bending directions in the bending section 30.2. Additional mechanisms can, however, be added to provide more bending directions by using the extra space available in the base 20. The actuation arrangement operates conceptually similarly to the previous design, with the addition of the pivot arm 85 shown in the figures. The actuators 41.2 are fixed at one end and the other end is fixed to connecting points 85.1 on the pivot arm 85. The angulation wires 41.1 protruding from the shaft are also connected to connecting points 85.2 on the pivot arm 85. In different embodiments, the connecting points for both the springs and the wires can be located at different positions along the arm 85 so as to increase or decrease the contraction length or bending amount produced. The pivot arm can serve to increase or decrease the effective actuation stroke of the actuators. The introduction of the pivot arm 85 therefore provides increased design and operational flexibility. Although not specifically shown in the drawings, the pivot arm 85 is also connected to a rotary measurement sensor, such as a potentiometer, that allows the control system of the bending mechanism to determine the current position of the bending section. This in turns allows the control system accurately to maintain a bending position. The introduction of the pivot arm 85 is therefore also beneficial from a control perspective.

Figure 15A:
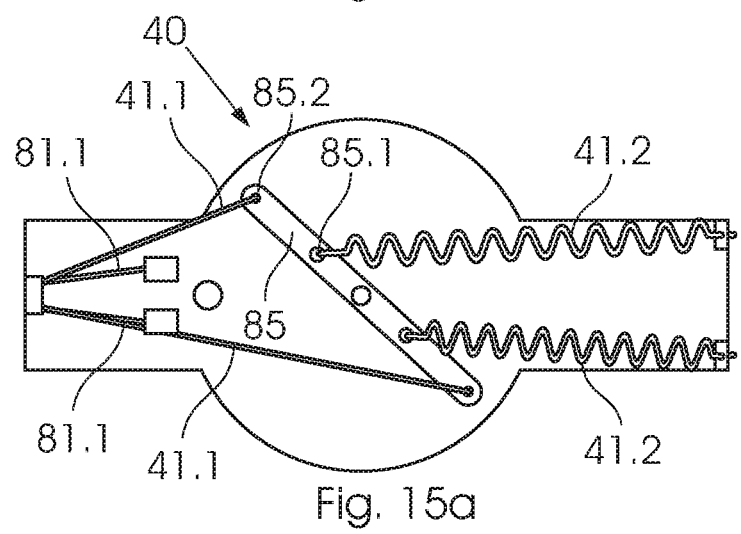
FIG. 15a is a plan view of the actuation arrangement of FIG. 14, with the bending section of the shaft in a bent position.
Figure 15B:
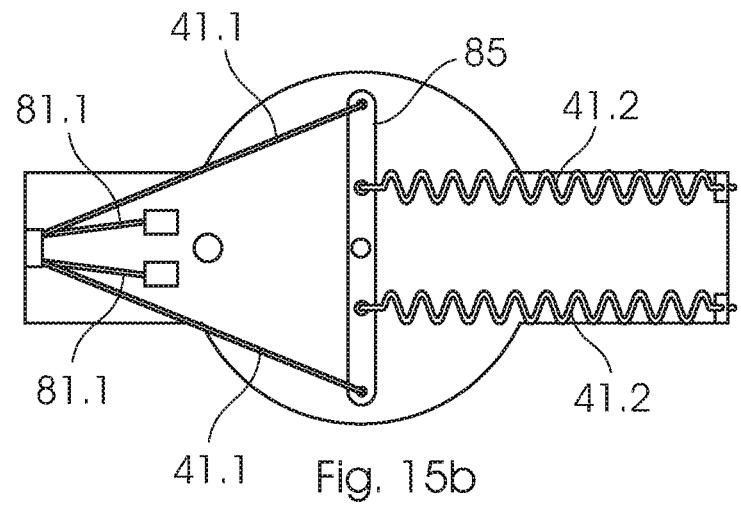
FIG. 15b is a plan view of the actuation arrangement of FIG. 14, with the bending section of the shaft in a straight position.

The bending operation of the mechanism is shown in FIGS. 15a and 15b. The operation performs in the same way as the previous design with the addition of the pivot arm 85. When an actuator 41.2 is activated, its contraction causes the pivot arm 85 to rotate in the direction of the contraction. Subsequently, the wire connection 85.2 on the corresponding side of the pivot arm 85 is pulled towards the actuated actuator, resulting in the bending of the bending section 30.2. The actuator 85 on the opposite side of the pivot arm 85 is extended when the arm 85 rotates, which also provides slack to the connection or angulation wire 41.1 on the non-contracting side. This ensures that an accurate and even bending motion is produced. To return to its previous position, or continue bending in the opposite direction, the extended actuator is actuated. The actuation arrangement 40 of the second embodiment is bulkier than that shown in the first embodiment, but important benefits are associated with the second arrangement that justifies the increase in size. It is, however, even more imperative in this case for the actuation arrangement 40, and in particular the actuators in the form of the SMA coils or springs 41.2, to be located in the base 20 of the device 10.

The invention seeks to address a number of market gaps by developing a reusable and mobile endoscopic system through several novel implementations. Although the invention is particularly useful for performing hysteroscopies, the application is by no means limited to hysteroscopies. In the case of a hysteroscopy, the invention is useable without the need for general anaesthesia by having an entirely flexible shaft with small outer diameters. This ensures minimal discomfort is experienced by the patient. It achieves this by implementing a novel bending mechanism that does not involve any motors, thereby reducing the size and cost while still allowing for bending to occur.

The invention is also reusable through the application of a disposable sterilized sheath, which provides the sterile environment for procedures while preventing the main reusable components from having to undergo damaging sterilization.

The mobility of the system is achieved by having a built-in camera and light source, while the visual interface is supplied by connecting the device to a smartphone or tablet.

Of particular importance is the smart bending mechanism used to control the bending of the flexible shaft. It implements a unique nickel-titanium alloy, also known as nitinol, spring that contracts like a muscle when an electrical current is supplied to it. Using these springs, the invention can produce the required bending motions to fully observe a cavity or organ. This spring system eliminates the need for motors and not only reduces the size of the device, but is considerably less costly than devices known in the art. The user controls and activates multiple springs separately, each for a specific direction. This allows the user to accurately bend the shaft up to 180° in four directions. Existing flexible endoscopes, and in particular hysteroscopes, are only capable of bending up to 110° in a single direction.

Another important aspect of the invention is that the actuation arrangement of the device in accordance with the invention is located in the base of the device, as opposed to the shaft or insertion section as has been proposed in the prior art. This is not a simple design choice, but was arrived at in order to achieve a number of important benefits. Some of these are listed below:

- Moving the actuation arrangement, and in particular the actuators or SMA coils, into the base allows for reducing the diameter of the shaft or insertion rod.
- The additional space available in the base allows for increased number and different lengths of actuators to be used. This allows the bending mechanism to produce a greater degree and complexity of bending motions.
- By placing the actuators in the base, the hollow diameter of the rod has additional space for channels and instrumentation.
- The activation of the actuators results in heat exposure to its surroundings. By placing the actuators in the base, it avoids exposing the working environment to heat generated when activating the actuators. The actuators can also be insulated more easily in the base.
- The design greatly simplifies fabrication and miniaturisation by reducing complexity of the shaft. Furthermore, shafts with functional differences (such as longer lengths, increased number of channels, etc.) can be swapped by disconnecting it from the base and reconnecting a different one.
- Placing the actuators in the base allows for increased contraction length and pulling force to be produced.
- The actuators, and in particular the two coils, act as opposing pairs. When one coil contracts, it pulls on and extends the coil on the opposite side. This ensures that slack is provided for the side of the bending tip not undergoing contraction and avoids causing buckling in the rod.

In summary, the inventors believe that the new device will present at least the following benefits over the prior art:

1. Reusable
   The main components of the system are reusable, with only a cheap sterile sheath being the disposable component. This is to prevent the entire system from having to undergo intense sterilization after use, which is potentially damaging and reduces its number of uses. By being reusable the invention also reduces the costs of procedures. The sheath also provides working channels for distention media and operative instruments, which allows for the same system to be used for both diagnostic and operative procedures.
2. Mobile
   The system implements a built-in CMOS camera and LED light source, eliminating the need for bulky additional equipment. The visual display component is provided by connecting the device to a smartphone, tablet, or laptop which are readily available and cheaper than the typical monitors used by existing technologies. The overall system is therefore highly portable.
3. Flexible
   The flexibility of the invention is crucial as it allows for successful procedures without general anaesthesia and outside of the operating theatre. The invention not only offers a completely flexible shaft portion but through a novel smart bending mechanism, allows the operator the control the bending motion to observe the entire uterine cavity. The system is therefore capable of bending up to 180° in 4 directions.
4. Accessibility
   Patient access to endoscopic procedures such as a hysteroscopy is greatly increased with the invention by not only reducing the costs involved but by allowing for procedures to take place outside of the operating room. Thereby allowing access to rural areas where hospitals are less equipped or for gynaecologists to perform in office procedures.

It will be appreciated that the above is only one embodiment of the invention and that there may be many variations without departing from the spirit and/or the scope of the invention. It is easily understood from the present application that the particular features of the present invention, as generally described and illustrated in the figures, can be arranged and designed according to a wide variety of different configurations. In this way, the description of the present invention and the related figures are not provided to limit the scope of the invention but simply represent selected embodiments.

The skilled person will understand that the technical characteristics of a given embodiment can in fact be combined with characteristics of another embodiment, unless otherwise expressed or it is evident that these characteristics are incompatible. Also, the technical characteristics described in a given embodiment can be isolated from the other characteristics of this embodiment unless otherwise expressed.

The invention claimed is:

1. An endoscopic device comprising:
   a base including a body and a handle;
   a shaft having a proximal end connected to the base; wherein the shaft is at least partially flexible and includes a bending section that is selectively displaceable between a straight configuration and a bent configuration; and
   an actuation arrangement for selectively displacing the bending section between the straight and bent configurations;
   wherein the actuation arrangement includes at least two actuators which are at least partially made from a shape memory alloy, and which are configured to displace the bending section of the shaft when electric current is passed therethrough;
   wherein the two actuators are configured to act as an opposing pair in order for one actuator to extend when the other actuator contracts, and
   wherein each actuator is located inside the base of the device, with at least one angulation wire extending from each actuator through the shaft towards the bending section in order for displacement of the actuator located inside the base to be transmitted to the bending section of the shaft.

2. The endoscopic device of claim 1, wherein the actuators are in the form of helical coils or springs made from a shape memory alloy.

3. The endoscopic device of claim 1, wherein a first end of the angulation wire is secured to or relative to the each of the actuators, and a second end of the angulation wire is secured to a distal end of the shaft.

4. The endoscopic device of claim 1, wherein a pivotable arm is located between the actuators and the angulation wires, and wherein an end of each actuator and an end of each angulation wire are secured to the pivotable arm in order for actuation of one of the actuators to result in displacement of the pivoting arm, with the pivotable arm in turn displacing the end of the angulation wire.

5. The endoscopic device of claim 4, wherein the pivotable arm is connected to a rotary measurement sensor that allows a control system of the bending mechanism to determine the current position of the bending section.

6. The endoscopic device of claim 5, wherein the rotary measurement sensor is a potentiometer.

7. The endoscopic device of claim 1, wherein a biasing means is located in the bending section in order to support the bending section and urge it towards an unbent configuration.

8. The endoscopic device of claim 7, wherein the biasing means is in the form of a helical spring.

9. The endoscopic device of claim 1, wherein the shaft includes a non-bending section which is at least partially flexible, and which can be configured between a flexible condition in which some flexibility is present in the non-bending section, and a stiff condition in which substantially no flexibility is present in the non-bending section.

10. The endoscopic device of claim 9, wherein at least one shape memory alloy stiffening wire extends from the base into and along the non-bending section, with an end of the stiffening wire being secured to an end of the non-bending section, in order for contraction of the stiffening wire to result in contraction of the non-bending section of the shaft, thus resulting in the non-bending section becoming rigid.

11. The endoscopic device of claim 1, further including a disposable sheath configured and dimensioned to fit around the shaft.

* * * * *